United States Patent
Chewter et al.

(10) Patent No.: US 8,822,710 B2
(45) Date of Patent: Sep. 2, 2014

(54) PROCESS FOR PREPARING AN EPOXIDE FROM AN OXYGENATE

(71) Applicant: Shell Oil Company, Houston, TX (US)

(72) Inventors: Leslie Andrew Chewter, Amsterdam (NL); Hervé Henry, Rotterdam (NL); Pieter Oldenhove, Amsterdam (NL); Rajaram Ramesh, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/653,116

(22) Filed: Oct. 16, 2012

(65) Prior Publication Data

US 2013/0096328 A1     Apr. 18, 2013

(30) Foreign Application Priority Data

Oct. 17, 2011   (EP) .................................. 11185461

(51) Int. Cl.
*C07D 301/02*     (2006.01)
*C07D 301/19*     (2006.01)

(52) U.S. Cl.
CPC .................................. *C07D 301/19* (2013.01)
USPC ......................................... 549/529; 549/518

(58) Field of Classification Search
USPC .................................................. 549/518, 529
See application file for complete search history.

(56) References Cited

U.S. PATENT DOCUMENTS

| | | | |
|---|---|---|---|
| 3,351,635 A | 11/1967 | Kollar | 260/348.5 |
| 5,210,354 A | 5/1993 | Dubner et al. | 585/469 |
| 2005/0250969 A1 | 11/2005 | Bridges | |
| 2006/0135833 A1 | 6/2006 | Malzkorn et al. | |

FOREIGN PATENT DOCUMENTS

| | | | | |
|---|---|---|---|---|
| WO | 2009065848 | 5/2009 | | |
| WO | 2009065898 | 5/2009 | | |
| WO | WO2009065848 | 5/2009 | | B01J 8/18 |
| WO | WO2009120290 | 10/2009 | | C07D 301/06 |

*Primary Examiner* — T. Victor Oh

(57) ABSTRACT

The invention relates to an integrated process for preparing an epoxide from an oxygenate, wherein the production of a lower olefin from the oxygenate and the subsequent epoxidation of the lower olefin is combined and wherein isobutene, a by-product of the lower olefin production, is converted into a hydroperoxide that is used for the conversion of the lower olefin into the corresponding epoxide.

16 Claims, 1 Drawing Sheet

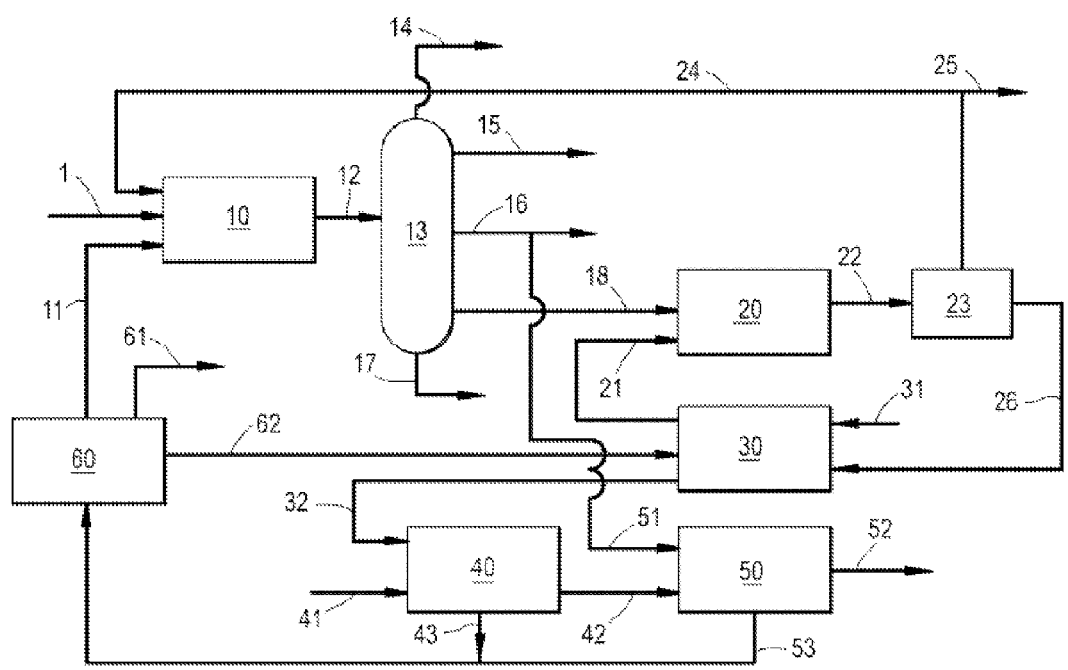

PROCESS FOR PREPARING AN EPOXIDE FROM AN OXYGENATE

This application claims the benefit of European Application No. 11185461.8 filed Oct. 17, 2011, which is incorporated herein by reference.

FIELD OF THE INVENTION

The invention relates to a process for preparing an epoxide from an oxygenate.

BACKGROUND TO THE INVENTION

Epoxides such as ethylene oxide and propylene oxide are important chemical intermediates. Propylene oxide is for example used as raw material for the production of polyether polyols, propylene glycol and glycol ethers. Ethylene oxide is for example used as raw material for the production of ethylene glycol, ethanolamines and acrylonitrile.

Epoxides are produced by epoxidation of olefins. Ethylene oxide is typically manufactured by direct oxidation of ethylene with oxygen. For propylene oxide, direct oxidation of propylene with oxygen has been proposed, for example in WO2009/120290. In practice, however, propylene is typically epoxidized to propylene oxide by reacting the propylene with an organic hydroperoxide, for example ethyl benzene hydroperoxide, tertiary butylhydroperoxide or cumene hydroperoxide. This is for example described in U.S. Pat. No. 3,351,635. An example of a commercially available epoxidation process that uses a hydroperoxide is the so-called SMPO process (styrene monomer propylene oxide process) wherein an ethyl benzene hydroperoxide is reacted with propylene to form methyl phenyl carbinol and propylene oxide. Methyl phenyl carbinol is subsequently dehydrated to styrene. Such process is for example disclosed in U.S. Pat. No. 5,210,354.

Conventionally, lower olefins such as ethylene and propylene are produced via steam cracking of hydrocarbon feedstocks including ethane, propane, naphtha, gasoil and hydrowax. An alternative route to lower olefins is the so-called oxygenate-to-olefin process. In such oxygenate-to-olefin process, an oxygenate such as methanol or dimethylether (DME) is provided to a reaction zone containing a suitable oxygenate conversion catalyst, typically a molecular sieve-comprising catalyst, and converted into ethylene and propylene. In addition to the desired lower olefins, a substantial part of the oxygenate is converted into C4+ olefins and paraffins.

In WO2009/065848 is disclosed an oxygenate-to-olefin process wherein the yield of lower olefins is increased by recycling a fraction comprising C4+ olefins to the reaction zone. At least part of the C4+ olefins in the recycle are converted into the desired lower olefins. A disadvantage of the process of WO2009/065848 is, however, that at least part of the recycle stream needs to be purged in order to avoid undesired accumulation of paraffins in the recycle stream. With the purge, also valuable C4+ olefins will be removed from the process without being converted into lower olefins.

Another disadvantage is that in an oxygenate-to-olefin process, less benzene is formed than in for example steam cracking of naphtha. If the lower olefins formed would then be converted into propylene oxide by an SMPO process, additional benzene would need to be imported and fed to the SMPO process.

SUMMARY OF THE INVENTION

It has now been found that the production of lower olefins and its subsequent epoxidation can be advantageously combined by converting isobutene, a by-product of the production of lower olefins, into a hydroperoxide that is used for the conversion of the lower olefins into the corresponding epoxides.

Accordingly, the present invention relates to a process for preparing an epoxide from an oxygenate, the process comprising the following steps:

a) contacting the oxygenate with a molecular sieve-comprising catalyst, at a temperature in the range of from 350 to 1000° C. to obtain an olefinic product stream comprising ethylene, propylene and a C4+ hydrocarbon fraction comprising C4+ paraffins and C4+ olefins including isobutene;

b) supplying at least part of the C4+ hydrocarbon fraction and methanol to an etherification reaction zone comprising an etherification catalyst and reacting, in the etherification reaction zone, at least part of the isobutene with an alcohol selected from the group consisting of methanol, ethanol and a mixture thereof to obtain an etherification product stream comprising an alkyl tert-butyl ether;

c) separating at least part of the etherification product stream into an alkyl tert-butyl ether-enriched stream and an isobutene-depleted C4+ hydrocarbon stream;

d) converting at least part of the alkyl tert-butyl ether in the alkyl tert-butyl ether-enriched stream into the alcohol and isobutane;

e) oxidizing isobutane obtained in step d) into tert-butyl hydroperoxide; and f) reacting tert-butyl hydroperoxide obtained in step e) with ethylene and/or propylene separated from the olefinic product stream obtained in step a) to obtain the epoxide and tertiary-butanol.

Thus, isobutene produced as by-product or intermediate product of the manufacture of lower olefins from oxygenates, is used for the manufacture of a hydroperoxide, i.e. tert-butylhydroperoxide, that is used for the epoxidation of lower olefins. In the epoxidation step, tertiary-butanol is produced that may advantageously be recycled to oxygenate conversion step a) and/or to alkyl tert-butyl ether conversion step d). Under the conditions prevailing in the oxygenate conversion step a), tertiary-butanol dehydrates into isobutene. If part of the tertiary-butanol is recycled to step d), it is preferred to dehydrate the tertiary-butanol to isobutene prior to recycling.

An advantage of the process according to the invention is that propylene oxide is formed as the only product. No major by-product, such as for example styrene in the SMPO process, is formed. A further advantage compared to an oxygenate-to-olefin step combined with the SMPO process, is that no additional feed stream (such as external benzene in a combined oxygenate-to-olefin/SMPO process) is needed.

BRIEF DESCRIPTION OF THE DRAWINGS

The FIGURE schematically shows a process according to the invention.

DETAILED DESCRIPTION OF THE INVENTION

In the process according to the invention, an oxygenate is first converted into lower olefins by contacting the oxygenate with a molecular sieve-comprising catalyst at a temperature in the range of from 350 to 1000° C. (oxygenate conversion step a)). Besides lower olefins, i.e. ethylene and propylene, C4+ hydrocarbons are formed as by-product. Thus, an olefinic product stream comprising ethylene, propylene and a C4+ hydrocarbon fraction comprising C4+ paraffins and C4+ olefins is obtained in step a). Typically, C4+ paraffins such as isobutane, n-butane, n-pentane, iso-pentane, and C4+ olefins such as isobutene, n-butenes, n-pentenes, iso-pentenes and C5+ naphtenes such as cyclopentane and cyclopentene will be present in the olefinic product stream. Small amounts of dienes like butadienes may be present in this stream.

Reference herein to an oxygenate is to a compound comprising at least one alkyl group that is covalently linked to an oxygen atom. Preferably, at least one alkyl group has up to five carbon atoms, more preferably up to four, even more preferably one or two carbon atoms, most preferably is methyl. Mono-alcohols and dialkylethers are particularly suitable oxygenates. Methanol and dimethylether or mixtures thereof are examples of particularly preferred oxygenates.

The oxygenate conversion in step a) is carried out by contacting the oxygenate with a molecular sieve-comprising catalyst at a temperature in the range of from 350 to 1000° C., preferably of from 350 to 750° C., more preferably of from 450 to 700° C., even more preferably of from 500 to 650° C. The conversion may be carried out at any suitable pressure, preferably at a pressure in the range of from 1 bar to 50 bar (absolute), more preferably of from 1 bar to 15 bar (absolute). A pressure in the range of from 1.5 to 4.0 bar (absolute) is particularly preferred.

Any molecular sieve comprising catalyst known to be suitable for the conversion of oxygenates, in particular alkanols and dialkylethers, into lower olefins may be used. Preferably the catalyst comprises a molecular sieve having a 8-, 10- or 12-ring structure and an average pore size in the range of from 3 Å to 15 Å. Examples of suitable molecular sieves are silicoaluminophosphates (SAPOs), aluminophosphates (AlPO), metal-substituted aluminophosphates or metal-substituted silicoaluminophosphates. Preferred SAPOs include SAPO-5, -8, -11, -17, -18, -20, -31, -34, -35, -36, -37, -40, -41, -42, -44, -47 and -56. SAPO-17, -18, -34, -35, and -44 are particularly preferred.

A particular suitable class of molecular sieves are zeolites. In particular in case not only oxygenates but also C4+ olefins or compounds that form C4+ olefins under the reaction conditions prevailing in oxygenate conversion step a), e.g. a tertiary alcohol or a tertiary alkylether such as tertiary-butanol or MtBE, a zeolite-comprising catalyst is preferred as molecular-sieve comprising catalyst, more preferably a catalyst comprising a zeolite with a 10-membered ring structure. Zeolite-comprising catalysts are known for their ability to convert higher olefins to lower olefins, in particular C4+ olefins to ethylene and/or propylene. Suitable zeolite-comprising catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48. Preferably, the catalyst comprises at least one zeolite selected from MFI, MEL, TON and MTT type zeolites, more preferably at least one of ZSM-5, ZSM-11, ZSM-22 and ZSM-23 zeolites.

The zeolite in the oxygenate conversion catalyst is preferably predominantly in the hydrogen form. Preferably at least 50 wt %, more preferably at least op wt %, even more preferably at least 95 wt %, still more preferably at least 100 wt % of the zeolite is in the hydrogen form.

The molecular sieve-comprising catalyst may further comprise a binder material such as for example silica, alumina, silica-alumina, titania, or zirconia, a matrix material such as for example a clay, and/or a filler.

The oxygenate conversion catalyst may comprise phosphorous as such or in a compound, i.e. phosphorous other than any phosphorous included in the framework of the molecular sieve. It is preferred that an MEL or MFI-type zeolites comprising catalyst additionally comprises phosphorous. The phosphorous may be introduced by pre-treating the MEL or MFI-type zeolites prior to formulating the catalyst and/or by post-treating the formulated catalyst comprising the MEL or MFI-type zeolites. Preferably, a catalyst comprising MEL or MFI-type zeolites comprises phosphorous as such or in a compound in an elemental amount of from 0.05-10 wt % based on the weight of the formulated catalyst. A particularly preferred catalyst comprises phosphor-treated MEL or MFI-type zeolites having SAR of in the range of from 60 to 150, more preferably of from 80 to 100. An even more particularly preferred catalyst comprises phosphor-treated ZSM-5 having SAR of in the range of from 60 to 150, more preferably of from 80 to 100.

In step a), not only lower olefins and C4+ hydrocarbons, but also water is formed. Water is typically separated from the olefinic product stream by means known in the art, for example by cooling the olefinic product stream in a water quench tower.

The olefinic product stream obtained may be fractionated by means known in the art into different fractions. Typically, the stream is fractionated in at least a fraction mainly comprising propylene and a C4+ hydrocarbon fraction. Usually, a fraction comprising mainly ethylene is first separated from the olefinic product stream in a deethaniser and a fraction mainly comprising propylene is separated from the bottoms of the de-ethaniser in a de-propaniser. The bottoms of the de-propaniser contains the C4+ hydrocarbon fraction.

In step b), at least part of the C4+ hydrocarbon fraction and an alcohol selected from the group consisting of methanol, ethanol and a mixture thereof are supplied to an etherification reaction zone comprising an etherification catalyst. Preferably, the part of the C4+ hydrocarbon fraction supplied to the etherification reaction zone is a stream mainly comprising C4 hydrocarbons that is separated from the bottoms of the de-propaniser in a de-butaniser. Optionally, the part of the C4+ hydrocarbon fraction that is supplied to the etherification reaction zone is first selectively hydrogenated in order to reduce any butadienes present. In the etherification reaction zone, at least part of the isobutene in the C4+ hydrocarbon fraction is reacted with the alcohol to obtain an etherification product stream comprising an alkyl tert-butyl ether. It will be appreciated that also further iso-olefins that may be present in the C4+ hydrocarbon fraction such as for example iso-amylenes (2-methyl-1-butene and 2-methyl-2-butene), will be etherified with the alcohol to the corresponding alkyl tert-alkyl ether.

Preferably, the alcohol is methanol and an etherification product stream comprising methyl tert-butyl ether is obtained.

Etherification of isobutene to form an alkyl tert-butyl ether is well-known in the art. Any catalyst and process conditions known to be suitable for such etherification may be used. Typically, the etherification catalyst is an acid catalyst. Preferably, the etherification catalyst is a protonated cation-exchange resin or a heteropolyacid promoted by a metal. A particularly preferred catalyst is Amberlyst-15.

Preferably, the etherification reaction is carried out at a temperature in the range of from 40 to 100° C., more preferably of from 50 to 85° C. The reaction may be carried out at any suitable pressure, preferably in the range of from 1 to 20 bar (absolute), more preferably of from 5 to 15 bar (absolute).

In step c), at least part of the etherification product stream is separated into an alkyl tert-butyl ether-enriched stream and an isobutene-depleted C4+ hydrocarbon stream. This may be done by any suitable means known in the art, for example by distillation.

At least part of the isobutene-depleted C4+ hydrocarbon stream obtained in step c) may be recycled to step a). In that case, preferably part of the isobutene-depleted C4+ hydrocarbon stream is purged from the process in order to avoid too much accumulation of paraffins in the recycle stream. An advantage of recycling the isobutene-depleted C4+ hydrocarbon stream obtained in step c) to step a) instead of recycling the C4+ hydrocarbon fraction obtained in step a) to step a) (as is done in the process disclosed in WO2009/0848) is that less valuable isobutene is purged from the recycle stream.

Instead of recycling part of the isobutene-depleted C4+ hydrocarbon stream to step a), it may be advantageous to subject this stream to an olefin cracking step wherein C4+ olefins in this stream are cracked to ethylene and propene. Olefin cracking is known in the art and is often applied to the C4+ effluent of an oxygenate-to-olefins process wherein a molecular sieve-comprising catalyst is used that does not or hardly catalyse the conversion of C4+ olefins to ethylene and propylene, such as for example SAPO-comprising catalysts. In a preferred embodiment of the invention, a SAPO-containing catalyst, more preferably a SAPO-34-containing catalyst, is used in step a) and at least part of the isobutene-depleted C4+ hydrocarbon stream is subjected to an olefin cracking step. Suitable catalysts and process conditions for olefin cracking are known in the art. Ethylene and propylene formed in the olefin cracking step is preferably combined with the olefinic product stream obtained in step a).

In step d) at least part of the alkyl tert-butyl ether in the alkyl tert-butyl ether-enriched stream is converted into the alcohol and isobutane. This may for example be done by first cracking alkyl tert-butyl ether into isobutene and the alcohol and then hydrogenating the isobutene thus-formed into isobutane. The cracking of an tertiary alkyl ether into its corresponding alcohol and iso-olefin and the hydrogenation of an iso-olefin into its corresponding iso-alkane are well-known in the art. The cracking and hydrogenation may be carried out in any suitable way known in the art. In the cracking step, preferably an acid catalyst is used. Preferred cracking catalysts include acid cation-exchange resins, heteropolyacids, metal oxides such as for example alumina or silica-alumina. The cracking is preferably carried out at a temperature in the range of from 100 to 250° C., more preferably of from 120 to 200° C. The pressure is preferably in the range of from 1 to 10 bar (absolute).

Alternatively and preferably, the alkyl tert-butyl ether is directly converted into isobutane and the alcohol, i.e. in a single step. The cracking and hydrogenation is then combined by contacting the alkyl tert-butyl ether with a hydrocracking catalyst in the presence of hydrogen. Any suitable hydrocracking catalyst may be used for this step. Such catalyst comprises a hydrogenating function, preferably a hydrogenating metal, supported on an acidic support material. Preferably, the catalyst comprises an acidic support material selected from zeolitic or amorphous silica alumina and alumina. Amorphous silica alumina is a particularly preferred support material. The hydrogenation function is preferably a hydrogenating metal selected from Group VIII metals, more preferably selected from Pt, Pd, Ru, Rh, Ir, Ni and combinations thereof. Hydrogenating metal that do not easily convert methanol into carbon monoxide and hydrogen under the hydrocracking conditions prevailing in this step are particularly preferred. Examples of such hydrogenating metals are Pt and a combination of Pt and Ru.

Step d) is preferably carried out at a temperature of at most 200° C. A higher temperature will result in a larger amounts of undesired by-products such as isobutene and dialkyl ether. More preferably, the temperature is in the range of from 50 to 200° C., even more preferably of from 60 to 180° C., still more preferably of from 80 to 150° C. A temperature in the range of from 85 to 120° C. is particularly preferred. Preferably, the pressure in step d) is such that the alkyl tert-butyl ether is predominantly, i.e. at least 80 wt %, preferably at least 90 wt %, in the liquid phase. Preferably, the total pressure in step d) is in the range of from 1 to 35 bar (absolute).

The methanol obtained in step d) is preferably recycled to step a) and/or to step b).

In step e), the isobutane obtained in step d) is oxidized into tert-butyl hydroperoxide. Such peroxidation step is well-known in the art.

In step f), the tert-butyl hydroperoxide obtained in step e) is reacted with ethylene and/or propylene separated from the olefinic product stream obtained in step a) to obtain the epoxide and tertiary-butanol. Such epoxidation step is well-known in the art. Preferably, the tert-butyl hydroperoxide is reacted with propylene to obtain propylene oxide.

In case propylene oxide is obtained in step f), the process according to the invention preferably further comprises converting the propylene oxide obtained in step f) into one or more polyether polyols, propylene glycol or propylene glycol ethers. Such conversion is known in the art and any suitable process conditions known in the art may be used. Polyether polyols can suitably be reacted with isocyanate to manufacture polyurethane.

The tertiary-butanol obtained in step f) is preferably kept in the process by recycling it to step a), or, after dehydration to isobutene, to alkyl tert-butyl ether conversion step d). Under the reaction conditions prevailing in step a), tertiary-butanol will be dehydrated and water and isobutene are formed. If the catalyst in step a) is able to catalyse conversion of isobutene into lower olefins, as is typically the case for a zeolite-comprising catalyst, in particular a catalyst comprising a zeolite with a 10-membered ring structure, part of the isobutene thus-formed will be further converted in lower olefins in step a). In order to maximize the propylene oxide yield of the process, it is, however, advantageous to keep a large part of the tertiary-butanol formed in the process as an iso-C4 compound that can easily be converted into isobutane. Such isobutane can then be peroxidised to the tert-butyl hydroperoxide that is needed for propylene oxide production in step f). Therefore, if the catalyst in step a) is able to convert isobutene into lower olefins, it is preferred to recycle at least part of the tertiary-butanol formed in step f), after dehydration of the tertiary-butanol to isobutene, as isobutene to alkyl tert-butyl ether conversion step d). More preferably, part of the butanol formed in step f) is recycled to step a) and part of the tertiary-butanol is recycled to step d). If recycled to both steps a) and d), the tertiary-butanol may be recycled to both steps in the form of isobutene, i.e. after dehydratation of the tertiary-butanol. Alternatively, it is recycled as tertiary-butanol to step a) and as isobutene to step d). The isobutene recycled to step d) will be hydrogenated to isobutane in step d). It will be appreciated that if step d) comprises separate cracking and hydrogenating steps, the isobutene will be recycled to the hydrogenating step.

Dehydration of tertiary-butanol to isobutene is well-known in the art. The dehydration of tertiary-butanol may be carried out using catalysts and process conditions known in the art.

Also in oxidation step e) tertiary-butanol is produced as by-product. The tertiary-butanol obtained in step e) may be recycled to step a) and step d) in the same way as the tertiary-butanol from step f).

DETAILED DESCRIPTION OF THE DRAWING

In the FIGURE, an embodiment of the invention is schematically shown. Methanol is fed via line 1 to oxygenate conversion reaction zone 10 comprising an oxygenate conversion catalyst. Recycled isobutene is co-fed to reaction zone 1 via line 11. In reaction zone 10, methanol is converted into olefins and an olefinic product stream is withdrawn from reaction zone 10 via line 12 and supplied to fractionation section 13. Fractionation section 13 comprises an de-ethaniser, a de-propaniser and a de-butaniser (not shown). The olefinic product stream is first fractionated by means of the deethaniser and depropaniser into an ethylene-rich stream, a propylene-rich stream, a C4+ hydrocarbon fraction and a lighter stream comprising light by-products such as methane and carbon oxides. The C4+ hydrocarbon fraction is further fractionated in the debutaniser into a C4 hydrocarbon fraction comprising isobutene and a fraction rich in C5+ hydrocarbons. The lighter stream, the ethylene-rich stream, the propylene-rich stream and the fraction rich in C5+ hydrocarbons are withdrawn from fractionation section 13 via lines 14, 15, 16 and 17, respectively. The C4 hydrocarbon fraction is fed via line 18 to etherification reaction zone 20. Methanol is supplied via line 21 to reaction zone 20 comprising an etherification catalyst. In etherification reaction zone 20, isobutene is reacted with methanol to form methyl tert-butyl ether (MtBE). The effluent of reaction zone 20 is via line 22 supplied to separator 23 to be separated into an isobutene depleted C4 hydrocarbon stream and an MtBE-enriched stream. The isobutene depleted C4 hydrocarbon stream is recycled to reaction zone 10 via line 24. To avoid undesired accumulation of saturated hydrocarbons, a small part of this stream is purged from the process via line 25. MtBE-enriched stream is withdrawn from separator 23 via line 26 and supplied to MtBE hydrocracking zone 30. Hydrogen is supplied to hydrocracking zone 30 via line 31. In zone 30, MtBE is converted into methanol and isobutane. Methanol is recycled to etherification zone 20 via line 21. Part of the methanol may be recycled to oxygenate conversion zone 10 (recycle not shown). Isobutane obtained in zone 30 is supplied via line 32 to oxidation reaction zone 40. Air is supplied as oxidant to zone 40 via line 41. In zone 40, isobutane is oxidised to tert-butyl hydroperoxide and tertiary-butanol. The tert-butyl hydroperoxide formed in zone 40 is supplied via line 42 to epoxidation zone 50. The tertiary-butanol formed is withdrawn via line 43. Part of the propylene-rich stream separated in fractionation section 13 from the olefinic product stream obtained in oxygenate conversion zone 10 is supplied to zone 50 via line 51. In zone 50, propylene oxide and tertiary-butanol are formed. Propylene oxide is withdrawn as product via line 52. The tertiary-butanol formed is withdrawn via line 53 and, combined with the tertiary-butanol in line 43, supplied to tertiary-butanol dehydration zone 60 and dehydrated into isobutene. Water is withdrawn from zone 60 via line 61. Part of the isobutene thus-formed is recycled to oxygenate conversion zone 10 via line 11 and part of the isobutene is recycled to MtBE hydrocracking zone 30 via line 62.

EXAMPLES

The invention is illustrated by the following non-limiting examples.

Example 1

Model calculations were carried out for a process configuration as shown in the FIGURE.

A stream of 3359 kilotons per annum (kton/a) of methanol, 114 kton/a of a recycle stream of isobutene and 350 kton/a of a recycle stream of isobutene-depleted C4 hydrocarbons are supplied to oxygenate conversion zone 10. Zone 10 contains a zeolitic catalyst comprising ZSM23 and ZSMS with a silica-to-alumina ratio of 280 in a weight ratio of 4 to 1. In zone 10, water and an olefinic product stream are formed. Fractionation yields 1146 kton/a of lower olefins, a C4 hydrocarbon fraction (293 kton/a) and a stream rich in C5+ hydrocarbons. The C4 hydrocarbon fraction and 65 kton/a of methanol (recycled from MtBE hydrocracking zone 30) is fed to etherification reaction zone 20 and MtBE is formed. After separation of the MtBE from the remaining C4 hydrocarbons, a stream of 350 kton/a of isobutene-depleted C4 hydrocarbons is recycled to zone 10. 179 kton/a of MtBE, 279 kton/a of isobutene from tertiary-butanol dehydration zone 60, and 17 kton/a of hydrogen are fed to MtBE hydrocracking zone 30 to form 500 kton/a of isobutane and 65 kton/a of methanol. The methanol is recycled to etherification reaction zone 20. The isobutane is supplied, together with air to oxidation reaction zone 40 to form tert-butyl hydroperoxide and tertiary-butanol. The tert-butyl hydroperoxide and 181 kton/a of the propylene produced in zone 10 are converted into 250 kton/a of propylene oxide in epoxidation zone 50. The tertiary-butanol formed in zones 40 and 50 is dehydrated in tertiary-butanol dehydration zone 60 to form 126 kton/a of water, and 393 kton/a of isobutene. Part of the isobutene (114 kton/a) is recycled to oxygenate conversion zone 10 and part (279 kton/a) is recycled to MtBE hydrocracking zone 30.

Example 2

Model calculations were carried out for a process configuration as in the FIGURE, but now with a direct recycle of all tertiary-butanol formed in isobutane oxidation zone 40 and epoxidation zone 50 to oxygenate conversion zone 10, i.e. without dehydration of tertiary-butanol to isobutene and without a recycle of tertiary-butanol to MtBE hydrocracking zone 30. Thus, all tertiary-butanol withdrawn from zones 40 and 50 via line 53 is recycled as tertiary-butanol to oxygenate conversion zone 10.

The amount of methanol fed to oxygenate conversion zone 10 is the same as in Example 1. In this configuration, less hydrogen is needed in MtBE hydrocracking zone 30, since no isobutene is recycled to this zone. As a result, less isobutane is formed in zone 30. Thus, less tert-butyl hydroperoxide is available for conversion into propylene oxide in epoxidation zone 50.

In the Table, the product streams in kilotons per day in the different lines with the reference numbers as in the FIGURE are given for EXAMPLE 1 and EXAMPLE 2. It will be appreciated that in EXAMPLE 2, tertiary-butanol is recycled to zone 10 and not isobutene (as in EXAMPLE 1 and the FIGURE).

TABLE 1

Product streams in kilotons per annum in EXAMPLES 1 and 2

| line | Compound | EXAMPLE 1 | EXAMPLE 2 |
| --- | --- | --- | --- |
| 1 | methanol | 3359 | 3359 |
| 31 | hydrogen | 17 | 4 |
| 32 | tertiary-butanol | 500 | 118 |
| 51 | propylene | 181 | 43 |
| 52 | propylene oxide | 250 | 59 |

TABLE 1-continued

Product streams in kilotons per annum in EXAMPLES 1 and 2

| line | Compound | EXAMPLE 1 | EXAMPLE 2 |
|---|---|---|---|
| 11 | isobutene | 114 | n.a. |
| 11 | tertiary-butanol | n.a. | 151 |
| 62 | isobutene | 279 | n.a. | n.a.: not applicable

Example 3

Co-Feeding Tertiary Butanol to Oxygenate-to-Olefins Conversion Step

This example illustrates that tertiary butanol recycled to an oxygenate conversion step a) comprising a catalyst comprising a zeolite with a 10-membered ring structure is converted into lower olefins.

Catalyst Preparation

Catalyst 1

A first catalyst (catalyst 1) was prepared as follows. ZSM-23 zeolite powder with a silica-to-alumina molar ratio (SAR) of 46, and ZSM-5 zeolite powder with a SAR of 80, both in the ammonium form, were mixed in a weight ratio of 1:1. Prior to mixing the powders, the ZSM-5 zeolite powder was treated with phosphorus. Phosphorus was deposited on the ZSM-5 zeolite powder by means of impregnation with an acidic solution containing phosphoric acid to obtain a phosphorous concentration of 2.0 wt %. The impregnated ZSM-5 powder was calcined at 550° C. The powder mixture was added to an aqueous solution to obtain a slurry and the slurry was milled Kaolin clay and a silica sol were added to the milled slurry and the resulting mixture was spray-dried. The weight-based average particle size of the spray-dried powder was between 70 and 90 μm. The spray-dried catalyst was exposed to ion-exchange using an ammonium nitrate solution. Phosphorus was deposited on the spray-dried catalyst by means of impregnation using an acidic solution containing phosphoric acid. The concentration of the solution was adjusted to impregnate 1.0 wt % of phosphorus on the catalyst. After impregnation the catalyst was dried at 140° C. and calcined at 550° C. for 2 hours. The catalyst thus obtained (40 wt % zeolite, 36 wt % kaolin clay and 24 wt % silica) is further referred to as catalyst 1.

Catalyst 2

A second catalyst (catalyst 2) was prepared as described hereinabove for catalyst 1, except that as zeolite powder only ZSM-5 with a SAR of 80 which was not treated with phosphorus prior to spray-drying, was used. After spray-drying, the concentration of the phosphorus impregnation solution was adjusted to impregnate 1.5 wt % of phosphorus on the spray-dried catalyst formulation. The final formulated catalyst thus obtained is further referred to as catalyst 2.

Oxygenate to Olefin Conversion

The conversion of tertiary butanol into olefins was tested by feeding different feed compositions with and without tertiary butanol to an oxygenate conversion catalyst (the tertiary butanol containing 20 wt % of isobutanol in order to make feeding as a liquid at room temperature possible). Three different feed compositions were used:

3 vol % tertiary butanol, balance $N_2$;
3 vol % tertiary butanol, 6 vol % methanol, balance $N_2$;
3 vol % 1-butene, 6 vol % methanol, balance $N_2$.

Each feed composition was tested over two different catalysts (catalysts 1 and 2) and at two different reaction temperatures (525 and 575° C.).

The experiments were carried out as follows. A sieve fraction of 60-80 mesh of catalyst was used, which was treated ex-situ in air at 550° C. for 2 hours. The catalyst was placed in a quartz reactor tube of 1.8 mm internal diameter. The catalyst was then heated under a flow of nitrogen to the reaction temperature and subsequently the feed composition was passed over the catalyst at atmospheric pressure (1 bar atmosphere). The gas hourly space velocity (GHSV), i.e. the total gas flow per gram of zeolite per hour, was 19,000 (ml·g zeolite$^{-1}$·h$^{-1}$). The effluent from the reactor was analyzed by gas chromatography (GC) to determine which products were formed. The effluent composition was calculated by the quotient of the mass of a specific product by the total mass of hydrocarbon products in the effluent. The results are shown in Table 2.

TABLE 2

Experiments performed with tertiary butanol

| Catalyst | Feed | T (° C.) | C2= (wt %) | C3= (wt %) | C4 (wt %) | C5 (wt %) | C6+ (wt %) | Light ends (wt %) | C4 sat/C4 total (wt/wt) |
|---|---|---|---|---|---|---|---|---|---|
| 1 | tC4OH | 575 | 7.42 | 19.98 | 68.13 | 3.01 | 1.24 | 0.22 | 1.43 |
| 1 | tC4OH/MeOH | 575 | 17.02 | 50.71 | 26.38 | 2.17 | 3.15 | 0.57 | 3.77 |
| 1 | C4=/MeOH | 575 | 17.54 | 52.08 | 25.38 | 1.80 | 2.58 | 0.61 | 2.23 |
| 2 | tC4OH | 575 | 12.15 | 30.85 | 51.86 | 2.28 | 2.54 | 0.32 | 2.73 |
| 2 | tC4OH/MeOH | 575 | 19.59 | 49.61 | 22.94 | 1.96 | 5.00 | 0.91 | 7.74 |
| 2 | C4=/MeOH | 575 | 20.76 | 50.88 | 21.45 | 1.87 | 4.32 | 0.72 | 4.42 |
| 1 | tC4OH | 525 | 7.64 | 28.32 | 55.58 | 5.92 | 2.49 | 0.06 | 2.59 |
| 1 | tC4OH/MeOH | 525 | 13.79 | 48.93 | 27.89 | 4.20 | 4.93 | 0.27 | 5.61 |
| 1 | C4=/MeOH | 525 | 14.28 | 51.47 | 26.30 | 3.32 | 4.39 | 0.23 | 3.37 |
| 2 | tC4OH | 525 | 12.26 | 39.47 | 40.85 | 3.84 | 3.35 | 0.23 | 4.31 |
| 2 | tC4OH/MeOH | 525 | 16.83 | 48.48 | 24.45 | 3.41 | 6.28 | 0.54 | 8.05 |
| 2 | C4=/MeOH | 525 | 17.04 | 50.45 | 23.85 | 3.21 | 5.15 | 0.31 | 5.25 | tC4OH: tertiary butanol; C4=: 1-butene; C2=: ethylene; C3=: propylene; C4 sat: saturated C4 hydrocarbons.

From the results shown in Table 2, it can be concluded that recycling of tertiary butanol to a 10-membered ring zeolite catalyst under oxygenate conversion conditions results in conversion of the tertiary butanol into lower olefins.

The above experiments were repeated, except that isobutanol was used instead of tertiary butanol. The results are shown in Table 3.

TABLE 3

Experiments performed with isobutanol

| Catalyst | Feed | T (° C.) | C2= (wt %) | C3= (wt %) | C4 total (wt %) | C5 total (wt %) | C6+ (wt %) | Light ends (wt %) | C4 sat/C4 total (wt/wt) |
|---|---|---|---|---|---|---|---|---|---|
| 1 | iC4OH | 575 | 8.37 | 22.81 | 64.73 | 2.86 | 1.15 | 0.09 | 1.36 |
| 1 | iC4OH/MeOH | 575 | 17.07 | 50.97 | 27.62 | 2.02 | 2.15 | 0.17 | 2.39 |
| 1 | C4=/MeOH | 575 | 16.07 | 52.81 | 26.81 | 1.95 | 2.06 | 0.29 | 1.72 |
| 2 | iC4OH | 575 | 12.91 | 32.65 | 49.65 | 2.05 | 2.48 | 0.25 | 3.01 |
| 2 | iC4OH/MeOH | 575 | 19.56 | 50.53 | 23.91 | 1.74 | 3.70 | 0.55 | 4.09 |
| 2 | C4=/MeOH | 575 | 18.16 | 51.93 | 23.62 | 1.63 | 3.88 | 0.77 | 2.64 |
| 1 | iC4OH | 525 | 8.30 | 30.58 | 52.70 | 5.64 | 2.75 | 0.03 | 2.72 |
| 1 | iC4OH/MeOH | 525 | 13.73 | 49.31 | 28.41 | 4.08 | 4.41 | 0.05 | 4.24 |
| 1 | C4=/MeOH | 525 | 13.16 | 50.98 | 27.91 | 3.97 | 3.95 | 0.04 | 2.93 |
| 2 | iC4OH | 525 | 13.16 | 41.77 | 37.70 | 3.62 | 3.57 | 0.17 | 5.08 |
| 2 | iC4OH/MeOH | 525 | 16.76 | 49.29 | 24.70 | 3.33 | 5.53 | 0.39 | 5.77 |
| 2 | C4=/MeOH | 525 | 15.94 | 50.68 | 24.54 | 3.11 | 5.15 | 0.58 | 4.09 | iC4OH: isobutanol; C4=: 1-butene; C2=: ethylene; C3=: propylene; C4 sat: saturated C4 hydrocarbons.

It can be seen by comparing Tables 2 and 3 that the results with isobutanol are comparable with the results with tertiary butanol. Also the results with 1-butene (C4=in Tables 2 and 3) are comparable with those with tertiary butanol or isobutanol. This indicates that the conversion of tertiary butanol in an oxygenate-to-olefins conversion step a) over a zeolitic catalyst goes via the conversion into isobutene and that isomerisation between isobutene and 1-butene occurs.

What is claimed is:

1. A process for preparing an epoxide from an oxygenate, the process comprising the following steps:
    a) contacting the oxygenate with a molecular sieve-comprising catalyst, at a temperature in the range of from 350 to 1000° C. to obtain an olefinic product stream comprising ethylene, propylene and a C4+ hydrocarbon fraction comprising C4+ paraffins and C4+ olefins including isobutene;
    b) supplying at least part of the C4+ hydrocarbon fraction and methanol to an etherification reaction zone comprising an etherification catalyst and reacting, in the etherification reaction zone, at least part of the isobutene with an alcohol selected from the group consisting of methanol, ethanol and a mixture thereof to obtain an etherification product stream comprising an alkyl tert-butyl ether;
    c) separating at least part of the etherification product stream into an alkyl tert-butyl ether-enriched stream and an isobutene-depleted C4+ hydrocarbon stream;
    d) converting at least part of the alkyl tert-butyl ether in the alkyl tert-butyl ether-enriched stream into the alcohol and isobutene via cracking and hydrogenation;
    e) oxidizing isobutane obtained in step d) into tert-butyl hydroperoxide; and
    f) reacting tert-butyl hydroperoxide obtained in step e) with ethylene and/or propylene separated from the olefinic product stream obtained in step a) to obtain the epoxide and tertiary-butanol.

2. A process according to claim 1, wherein at least part of the isobutene-depleted C4+ hydrocarbon stream obtained in step c) is recycled to step a).

3. A process according to claim 1, wherein the molecular sieve-containing catalyst is a zeolite-comprising catalyst.

4. A process according to claim 3, wherein the zeolite-comprising catalyst comprises at least one zeolite selected from MFI, MEL, TON and MTT type zeolites.

5. A process according to claim 4, wherein the zeolite-comprising catalyst comprises at least one of ZSM-5, ZSM-11, ZSM-22 and ZSM-23 zeolites.

6. A process according to claim 1, further comprising the following step:
    g) recycling at least part of the tertiary-butanol obtained in step f) to step a and/or to step d).

7. A process according to claim 1, wherein tertiary-butanol is co-produced in step e) and wherein tertiary-butanol produced in step e) is recycled to step a) and/or to step d).

8. A process according to claim 6, wherein the tertiary-butanol recycled to step d) is dehydrated prior to recycling to step d).

9. A process according to claim 7, wherein the tertiary-butanol recycled to step d) is dehydrated prior to recycling to step d).

10. A process according to any claim 1, wherein the oxygenate is selected from the group consisting of alkanols and di-alkylethers having up to five carbon atoms.

11. A process according to claim 10, where the oxygenate is methanol, dimethylether, or a mixture thereof.

12. A process according to claim 1, wherein in step d) the alkyl tert-butyl ether is first converted by cracking into isobutene and the alcohol and the isobutene is then hydrogenated into isobutane.

13. A process according to claim 1, wherein in step d) the alkyl tert-butyl ether is directly converted into isobutane and the alcohol by contacting alkyl tert-butyl ether with a hydrocracking catalyst in the presence of hydrogen.

14. A process according to claim 1, wherein the alcohol obtained in step d) is recycled to step a) and/or to step b).

15. A process according to claim 1, wherein the reacting in step b) is carried out at a temperature in the range of from 30 to 100° C.

16. A process according to claim 1, wherein the etherification catalyst is a protonated cation-exchange resin.

* * * * *